United States Patent
Asari et al.

(10) Patent No.: US 9,289,386 B2
(45) Date of Patent: *Mar. 22, 2016

(54) ORAL FILM-FORM BASE AND ORAL FILM-FORM PREPARATION

(75) Inventors: Daisuke Asari, Ibaraki (JP); Mitsuhiko Hori, Ibaraki (JP); Keiko Ogawa, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/146,829

(22) PCT Filed: Mar. 6, 2009

(86) PCT No.: PCT/JP2009/054335
§ 371 (c)(1),
(2), (4) Date: Jul. 28, 2011

(87) PCT Pub. No.: WO2010/087032
PCT Pub. Date: Aug. 5, 2010

(65) Prior Publication Data
US 2011/0293673 A1    Dec. 1, 2011

(30) Foreign Application Priority Data
Jan. 29, 2009 (WO) .................. PCT/JP2009/051511

(51) Int. Cl.
*A61K 9/00* (2006.01)
*A61K 9/70* (2006.01)
*A61K 47/26* (2006.01)
*A61K 47/38* (2006.01)

(52) U.S. Cl.
CPC ............. *A61K 9/0056* (2013.01); *A61K 9/7007* (2013.01); *A61K 47/26* (2013.01); *A61K 47/38* (2013.01)

(58) Field of Classification Search
CPC ..... A61K 47/26; A61K 47/38; A61K 9/0056; A61K 9/7007
See application file for complete search history.

(56) References Cited

U.S. PATENT DOCUMENTS

| 4,292,426 | A | 9/1981 | Orii et al. |
|---|---|---|---|
| 4,639,368 | A | 1/1987 | Niazi et al. |
| 4,687,660 | A | 8/1987 | Baker et al. |
| 5,641,637 | A | 6/1997 | Hudak et al. |
| 5,948,430 | A | 9/1999 | Zerbe et al. |
| 6,156,343 | A | 12/2000 | Morita et al. |
| 6,455,053 | B1 | 9/2002 | Okada et al. |
| 6,531,151 | B1 * | 3/2003 | Besse .............. 424/464 |
| 6,649,186 | B1 | 11/2003 | Robinson et al. |
| 2001/0006677 | A1 | 7/2001 | McGinity et al. |
| 2003/0099690 | A1 | 5/2003 | Awamura et al. |
| 2005/0008735 | A1 | 1/2005 | Pearce |
| 2005/0079138 | A1 * | 4/2005 | Chickering et al. ............. 424/46 |
| 2005/0147653 | A1 | 7/2005 | Yasuda et al. |
| 2005/0163830 | A1 | 7/2005 | Rademacher et al. |
| 2005/0175675 | A1 | 8/2005 | Seibertz |
| 2005/0186257 | A1 | 8/2005 | Manegold et al. |
| 2005/0208110 | A1 | 9/2005 | Singh et al. |
| 2006/0052340 | A1 | 3/2006 | Tsuzuki et al. |
| 2006/0078597 | A1 | 4/2006 | Jentzsch et al. |
| 2007/0098790 | A1 | 5/2007 | Jiang |
| 2007/0122455 | A1 | 5/2007 | Myers et al. |
| 2007/0178055 | A1 | 8/2007 | Buch et al. |
| 2007/0237871 | A1 | 10/2007 | Furusawa |
| 2007/0281003 | A1 | 12/2007 | Fuisz et al. |
| 2007/0298105 | A1 * | 12/2007 | Hwang .......................... 424/468 |
| 2008/0003267 | A1 | 1/2008 | Spencer et al. |
| 2008/0200452 | A1 | 8/2008 | Obermeier et al. |
| 2008/0268027 | A1 | 10/2008 | Yang et al. |
| 2009/0155351 | A1 | 6/2009 | Hejl et al. |
| 2009/0196908 | A1 | 8/2009 | Lee et al. |
| 2009/0317531 | A1 | 12/2009 | Reh et al. |
| 2010/0150986 | A1 | 6/2010 | Nagaso et al. |
| 2011/0054043 | A1 | 3/2011 | Funaki et al. |
| 2011/0111037 | A1 | 5/2011 | Boit et al. |
| 2011/0182993 | A1 | 7/2011 | Asari et al. |

(Continued)

FOREIGN PATENT DOCUMENTS

| CA | 1 067 407 | 12/1979 |
|---|---|---|
| CA | 2 339 836 A1 | 3/2000 |

(Continued)

OTHER PUBLICATIONS

Chinese Office Action issued in Application No. 200980155744.8 dated Mar. 22, 2012.
Fourth Notification of Office Action issued by The State Intellectual Property Office of China in counterpart CN Application No. 200980155744.8, dated Oct. 11, 2013.
Supplementary European Search Report issued in counterpart EP Application No. 09839222.8, dated Jul. 26, 2013.
Third Notification of Office Action issued by the State Intellectual Property Office of China in counterpart CN Application No. 200980155744.8 dated Apr. 1, 2013.
Russian Office Action issued in Application No. 2011135837 dated Sep. 19, 2012.
Office Action issued by State Intellectual Property Office of China in corresponding CN application 200980155744.8 dated Dec. 12, 2012.
Office Action, dated Aug. 27, 2013, issued by the Japanese Patent Office, in counterpart Application No. 2010-548356.
Office Action, dated Feb. 12, 2014, issued by the Japanese Patent Office, in counterpart Application No. 2010-548356.

(Continued)

*Primary Examiner* — Suzanne Ziska
(74) *Attorney, Agent, or Firm* — Sughrue Mion, PLLC (57) ABSTRACT

The present invention provides a film-form base having one or more sugars or sugar alcohols dispersed as fine particles therein, and also provides a film-form preparation containing the base and a drug. The base is produced by dispersing, in an organic solvent having a solubility parameter of 9.7 or higher, an edible polymer soluble in water and the organic solvent, and particles of one or two or more compounds selected from the group consisting of mono- to hexasaccharide sugars and sugar alcohols thereof which have an average particle size of 0.1 μm to 60 μm and are insoluble in an organic solvent. The present invention can therefore provide oral film-form base and preparation which have a rapid dissolution profile in the mouth and sufficient film strength, and provide a reduced sticky sensation attributed to the water-soluble polymer in the mouth and an improved feel when handled with the fingers.

11 Claims, 3 Drawing Sheets

(56) References Cited

U.S. PATENT DOCUMENTS

| | | | |
|---|---|---|---|
| 2011/0293673 A1 | 12/2011 | Asari et al. | |
| 2011/0293720 A1 | 12/2011 | General et al. | |
| 2011/0305768 A1* | 12/2011 | Mao et al. | 424/499 |

FOREIGN PATENT DOCUMENTS

| | | |
|---|---|---|
| CN | 1652824 A | 8/2005 |
| CN | 101287445 A | 10/2008 |
| CN | 102300565 A | 12/2011 |
| EP | 1 522 225 A1 | 4/2005 |
| EP | 1 752 127 A1 | 2/2007 |
| FR | 2933299 A1 | 1/2010 |
| JP | 51-29218 | 3/1976 |
| JP | 7-187993 A | 7/1995 |
| JP | 10-179045 A | 7/1998 |
| JP | 11-116465 A | 4/1999 |
| JP | 11-116469 A | 4/1999 |
| JP | 2001-288074 A | 10/2001 |
| JP | 2001-318348 | 11/2001 |
| JP | 2002-523359 T | 7/2002 |
| JP | 2004-43450 A | 2/2004 |
| JP | 3496727 B2 | 2/2004 |
| JP | 2005-008568 | 1/2005 |
| JP | 2005-21124 A | 1/2005 |
| JP | 2005-060244 A | 3/2005 |
| JP | 2005-511522 A | 4/2005 |
| JP | 2005-517722 A | 6/2005 |
| JP | 2005-342154 A | 12/2005 |
| JP | 2005-536443 A | 12/2005 |
| JP | 2005-537233 A | 12/2005 |
| JP | 2006-513269 | 4/2006 |
| JP | 2007-500252 | 1/2007 |
| JP | 2007-509172 A | 4/2007 |
| JP | 2007-528876 A | 10/2007 |
| JP | 2008-517935 A | 5/2008 |
| JP | 2008-169138 A | 7/2008 |
| JP | 2009-507854 | 2/2009 |
| JP | 2009-510136 A | 3/2009 |
| JP | 2010-158173 A | 7/2010 |
| JP | 2010-172256 A | 8/2010 |
| JP | 2010-209104 A | 9/2010 |
| JP | 4597662 B2 | 12/2010 |
| JP | 2001-504106 A | 3/2011 |
| JP | 2011-153113 A | 8/2011 |
| WO | 98/20862 A1 | 5/1998 |
| WO | 03/030882 A1 | 4/2003 |
| WO | 03/030883 A1 | 4/2003 |
| WO | 03/070227 A1 | 8/2003 |
| WO | 03/101420 A1 | 12/2003 |
| WO | 2004/047794 A2 | 6/2004 |
| WO | 2004/066986 A1 | 8/2004 |
| WO | 2004/080499 A1 | 9/2004 |
| WO | 2005/039499 A2 | 5/2005 |
| WO | 2005/082048 A2 | 9/2005 |
| WO | 2006/031209 A1 | 3/2006 |
| WO | 2006/047365 A1 | 5/2006 |
| WO | 2006/114604 A2 | 11/2006 |
| WO | 2007/009801 A2 | 1/2007 |
| WO | 2007/030754 A2 | 3/2007 |
| WO | 2007/038926 A1 | 4/2007 |
| WO | 2008/089151 A2 | 7/2008 |
| WO | 2008/149440 A1 | 12/2008 |
| WO | 2009/099830 | 8/2009 |
| WO | 2009/128433 A1 | 10/2009 |
| WO | 2010/015713 A1 | 2/2010 |
| WO | 2010/086989 A1 | 8/2010 |
| WO | 2010/144817 A1 | 12/2010 |

OTHER PUBLICATIONS

Third Party Observation issued in JP Application No. 2010-548356, notified on Dec. 24, 2013.

Office Action dated Mar. 10, 2015, issued by the Canadian Intellectual Property Office in counterpart Canadian application No. 2,750,617.

European Search Report issued in EP Application No. 13000089.6, dated Jul. 12, 2013, which corresponds to U.S. Appl. No. 13/737,255.

Office Action dated Apr. 21, 2015 from the Japanese Patent Office in application No. 2012-003625, which corresponds to U.S. Appl. No. 13/737,255.

Decision of Refusal dated Jan. 13, 2015, issued by the Japanese Patent Office in Japanese application No. 2011-049504, which corresponds to U.S. Appl. No. 13/073,022.

Office Action dated Aug. 26, 2014, issued by the Japanese Patent Office in Application No. 2011-049504, which corresponds to U.S. Appl. No. 13/073,022.

Office Action dated May 22, 2014, issued by the State Intellectual Property Office of China in Chinese Application No. 201110078800.1, which corresponds to U.S. Appl. No. 13/073,022.

Office Action dated Mar. 19, 2015, issued by the Russian Patent Office in Application No. 2011111666/15 which corresponds to U.S. Appl. No. 13/073,022.

Second Notification of Office Action issued by The State Intellectual Property Office of China in CN Application No. 201110078800.1, dated Nov. 13, 2013, which corresponds to U.S. Appl. No. 13/073,022.

Decision of Refusal issued by The State Intellectual Property Office of China in CN Application No. 201110078800.1, dated Nov. 3, 2014, which corresponds to U.S. Appl. No. 13/073,022.

Second Office Action dated Jan. 17, 2014, issued by the State Intellectual Property Office of the People's Republic of China in Application No. 201110030217.3, which corresponds to U.S. Appl. No. 13/014,245.

Second Office Action dated Jan. 23, 2014, issued by the State Intellectual Property Office of the People's Republic of China in Application No. 201110078784.6, which corresponds to U.S. Appl. No. 13/072,972.

Decision of Refusal dated Aug. 11, 2014, issued by the State Intellectual Property Office of the People's Republic of China in Application No. 201110030217.3, which corresponds to U.S. Appl. No. 13/014,245.

First Office Action dated May 21, 2013, issued by the State Intellectual Property Office of the People's Republic of China in Application No. 201110030217.3, which corresponds to U.S. Appl. No. 13/014,245.

Extended European Search Report dated Apr. 20, 2011, issued in EP Application No. 11000618.6, which corresponds to U.S. Appl. No. 13/014,245.

European Office Action dated Nov. 2, 2012, issued in EP Application No. 11000618.6, which corresponds to U.S. Appl. No. 13/014,245.

First Notification of Office Action dated Apr. 1, 2013 issued by the State Intellectual Property Office of the People's Republic of China in counterpart Application No. 201110078800.1, which corresponds to U.S. Appl. No. 13/073,022.

Journal of Nanjing College of Traditional Chinese Medicine, 1984, No. 4, pp. 53-55.

European Office Action dated May 10, 2012 issued in EP Application No. 11002555.8, which corresponds to U.S. Appl. No. 13/073,022.

The United States Pharmacopeia USP 24, The National Formulary NF 19, Jan. 1, 1999, p. 10 (XP55026035).

European Search Report dated Jun. 29, 2011, issued in EP Application No. 11002555.8, which corresponds to U.S. Appl. No. 13/073,022.

Nasirov et al., Anabasne hydrochloride—A New Antismoking agent, New Drugs, 1978, pp. 281-283.

Kollidon, BASF, 1998, pp. 35-36.

ToxNet (http://toxnet.nlm.nih.gov/cgi-bin/sis/search/a?dbs+hsdb:@term+@DOCNO+783, accessed Aug. 17, 2013).

Office Action dispatched on Dec. 17, 2013, issued in JP Application No. 2010-079429, which corresponds to U.S. Appl. No. 13/072,972.

First Notification of Office Action dated May 23, 2013, issued by the State Intellectual Property Office of the People's Republic of China in Application No. 201110078784.6, which corresponds to U.S. Appl. No. 13/072,972.

Office Action dated Mar. 28, 2011, issued by the Russian Patent Office in Application No. 20111116665, which corresponds to U.S. Appl. No. 13/072,972.

(56) References Cited

OTHER PUBLICATIONS

Stankovic, Ivan, Pullulan Chemical and Technical Assessment, Clinical and Technical Assessment 65$^{th}$ JECFA, 2002, pp. 1-8.

Perfetti et al., Influence of Polymer Coating on Strength of Particles: Polymer and Environmental Parameters, BioPowders Mini-Conference-Budapest, 2007, pp. 76-87.

Llianas et al., Diclofenac Solubility: Independent Determination of the Intrinsic Solubility of Three Crystal Forms, J. Med. Chem., 2007, 50, pp. 979-983.

Extended European Search Report dated Jul. 4, 2011, issued in EP Application No. 11002556.6, which corresponds to U.S. Appl. No. 13/072,972.

Developing Solid Oral Dosage Forms: Pharmaceutical Theory & Practice (edited by Qiu et al, Elvisar, 2009).

Sigma Aldrich L-ascorbic acid.

U.S. Non-Final Office Action dated Jan. 5, 2016, issued by the USPTO in U.S. Appl. No. 13/737,255.

\* cited by examiner

ORAL FILM-FORM BASE AND ORAL FILM-FORM PREPARATION

CROSS REFERENCE TO RELATED APPLICATIONS

This application is a National Stage of International Application No. PCT/JP2009/054335 filed on Mar. 6, 2009, which claims priority from International Application No. PCT/JP2009/051511, filed on Jan. 29, 2009, the contents of all of which are incorporated herein by reference in their entirety.

TECHNICAL FIELD

The present invention relates to an oral film-form base that readily dissolves in the mouth; and a preparation containing a drug in the base. More specifically, the present invention relates to an oral film-form base and a preparation that will dissolve rapidly in the mouth such that the drug will be well absorbed via the gastrointestinal tract or oral mucosa.

BACKGROUND ART

At present, orally administered drugs are marketed as solid preparations such as uncoated tablets, coated tablets, capsules, powders, and granules; liquid preparations such as liquids and emulsions; and the like. Orally disintegrating tablets and rapidly dissolving oral films are already on the market as preparations that disintegrate in the mouth and are absorbed by the gastrointestinal tract.

Orally administered film-, tape-, or sheet-form preparations that are to be disintegrated or dissolved by saliva without being chewed are already available as ten or more over-the-counter drugs (OTC drugs) overseas. In Japan, those preparations are available as one ethical pharmaceutical, as well as over-the-counter drugs.

The following Patent Documents teach technologies relating to such film-form preparations. Patent Document 1 discloses a base for a preparation which is obtained by dissolving, in a solvent, hydroxypropyl cellulose or a mixture of hydroxypropyl cellulose with polyvinylpyrrolidone, and a tannin substance, and then removing the solvent. Patent Document 2 discloses a film-form troche which is obtained by laminating a coating layer (a) containing a water-soluble, non-hygroscopic polysaccharide and a softener, a drug layer (b) containing a drug and an edible water-soluble polymer, and a drug layer (c) containing a drug, an edible water-soluble polymer, and a tannin substance in the order of (a), (b), (c), (b), and (a). Patent Document 3 discloses a rapidly dissolving film-form preparation which contains a drug and an edible polymer substance, has a film breaking strength of 200 to 3000 g/$\phi$ 7 mm and a film tensile strength of 200 to 3000 g/15 mm, and melts within 60 seconds in the mouth. Patent Document 4 discloses an oral film preparation that contains one of a pregelatinized starch and pullulan; an enzyme-modified starch; and a plasticizer. Patent Document 5 discloses a soluble film preparation which contains an active ingredient having a water solubility of about less than 1 g/4 mL at room temperature, and has a moisture content of about less than 15 wt %. Patent Document 6 discloses a film-form preparation which contains a drug, an edible water-soluble film forming agent, and low-substituted hydroxypropyl cellulose with a molar substitution degree of 0.05 to 1.0. Also, Patent Document 7 discloses a technology of preparing a rapidly dissolving preparation, which rapidly disintegrate or dissolve in the mouth or the like, by dissolving or dispersing a drug, saccharides, and polyvinylpyrrolidone in an organic solvent, and then removing the organic solvent.

However, the film-form bases and preparations having been disclosed up to now are produced by dispersing or dissolving a drug in a water-soluble polymer and, sugars or sugar alcohols are used for some of those bases and preparations (Patent Document 3 and Patent Document 4). In production of such bases or preparations, sugars or sugar alcohols to be used are in the dissolved in a solvent or recrystallized. For this reason, those conventional oral film-form bases or preparations give a sticky sensation attributed to the water-soluble polymer when applied in the mouth or when handled with the fingers. Patent Document 7, which relates to a rapidly dissolving preparation, teaches neither a technology of dispersing fine particles of saccharides nor production of a film-form preparation.

Patent Document 1: JP 7-187993 A
Patent Document 2: JP 2001-288074 A
Patent Document 3: JP 2004-43450 A
Patent Document 4: JP 2005-21124 A
Patent Document 5: JP 2007-528876 T
Patent Document 6: JP 2008-169138 A
Patent Document 7: JP 11-116465 A

DISCLOSURE OF THE INVENTION

Problems to be Solved by the Invention

To solve such problems, the present invention aims to provide oral film-form base and preparation which have a rapid dissolution profile in the mouth and sufficient film strength, and provide a reduced sticky sensation attributed to the water-soluble polymer in the mouth and an improved feel when handled with the fingers.

Means for Solving the Problems

The present inventors have made various studies to solve the above problems, and have found that a preparation, if produced using the following film-form base, has a rapid dissolution profile in the mouth and sufficient film strength, and provides a reduced sticky sensation attributed to the water-soluble polymer in the mouth and an improved feel when handled with the fingers. The film-form base is produced by dispersing, in an organic solvent having a solubility parameter of 9.7 or higher, an edible polymer soluble in water and the organic solvent, and particles of one or more compounds of sugars and sugar alcohols thereof as fine particles which are insoluble in the organic solvent.

That is, the present invention relates to the following [1] to [11].

[1] An oral film-form base comprising one or two or more edible polymers soluble in water and an organic solvent having a solubility parameter of 9.7 or higher, and particles of one or two or more compounds selected from the group consisting of mono- to hexasaccharide sugars and sugar alcohols thereof, having an average particle size of 0.1 μm to 60 μm.

[2] The oral film-form base according to [1], wherein the particles of one or two or more compounds selected from the group consisting of sugars and sugar alcohols thereof have an average particle size of 0.1 μl to 30 μm.

[3] The oral film-form base according to [1] or [2], wherein the edible polymers soluble in water and an organic solvent having a solubility parameter of 9.7 or higher are one or two or more compounds selected from the group consisting of polyvinylpyrrolidone and hydroxypropyl cellulose.

[4] The oral film-form base according to [3], wherein polyvinylpyrrolidone has a weight-average molecular weight of 2,500 to 3,000,000.

[5] The oral film-form base according to [3], wherein hydroxypropyl cellulose has a weight-average molecular weight of 10,000 to 1,200,000.

[6] The oral film-form base according to [3] or [5], wherein hydroxypropyl cellulose has a hydroxypropoxy substitution degree of 50% to 100%.

[7] An oral film-form preparation comprising a drug in the oral film-form base according to any one of [1] to [6].

[8] A method of producing an oral film-form base, comprising dissolving or dispersing, in an organic solvent having a solubility parameter of 9.7 or higher, one or two or more edible polymers soluble in water and the organic solvent, and particles of one or two or more compounds selected from the group consisting of mono- to hexasaccharide sugars and sugar alcohols thereof, having an average particle size of 0.1 μm to 60 μm, and forming a thin layer of the resulting dispersion and then drying the layer.

[9] A method of producing an oral film-form preparation, comprising dissolving or dispersing, in an organic solvent having a solubility parameter of 9.7 or higher, a drug, one or two or more edible polymers soluble in water and the organic solvent, and particles of one or two or more compounds selected from the group consisting of mono- to hexasaccharide sugars and sugar alcohols thereof, having an average particle size of 0.1 μm to 60 μm, and forming a thin layer of the resulting dispersion, and then drying the layer.

[10] A method of producing an oral film-form base, comprising: dissolving, in a portion of an organic solvent having a solubility parameter of 9.7 or higher, one or two or more edible polymers soluble in water and the organic solvent to prepare a solution; mixing the solution with a dispersion prepared by dispersing, in the rest of the organic solvent having a solubility parameter of 9.7 or higher, particles of one or two or more compounds selected from the group consisting of mono- to hexasaccharide sugars and sugar alcohols thereof, having an average particle size of 0.1 μm to 60 μm, to prepare a mixed dispersion; and forming a thin layer of the dispersion, and then drying the layer.

[11] A method of producing an oral film-form preparation, comprising: dissolving, in a portion of an organic solvent having a solubility parameter of 9.7 or higher, one or two or more edible polymers soluble in water and the organic solvent to prepare a solution; mixing the resulting solution with a dispersion prepared by dissolving or dispersing, in the rest of the organic solvent having a solubility parameter of 9.7 or higher, a drug and particles of one or two or more compounds selected from the group consisting of mono- to hexasaccharide sugars and sugar alcohols thereof, having an average particle size of 0.1 μm to 60 μm, to prepare a mixed dispersion; and forming a thin layer of the dispersion, and then drying the layer.

Effect of the Invention

The oral film-form base and preparation according to the present invention each have one or two or more compounds selected from sugars and sugar alcohols dispersed as particles therein, and have a rapid solubility profile and sufficient film strength. Further, the base and the preparation provide clearly improved properties, such as a reduced sticky sensation attributed to the water-soluble polymer when applied in the mouth and an improved feel when handled with the fingers, compared to the conventional products. That is, in the case that the base and the preparation are produced by uniformly dispersing one or two or more compounds selected from sugars and sugar alcohols as particles in a film, the base and the preparation can clearly improve only the properties relating to the taking of the base and the preparation, such as oral dissolution, the feel of the film in the mouth, and the feel when handled with the fingers, without deteriorating the film properties required as the base and the preparation, such as tensile strength and stiffness.

EXPLANATION OF SYMBOLS

1a Particles of one or two or more compounds selected from the group consisting of mono- to hexasaccharide sugars and sugar alcohols thereof
1b Film containing edible polymer, or edible polymer and drug
2a Probe
2b Double-sided tape
2c Test piece
2d Collagen film
2e Rubber
2f Test platform

MODE(S) FOR CARRYING OUT THE INVENTION

Figure 1:
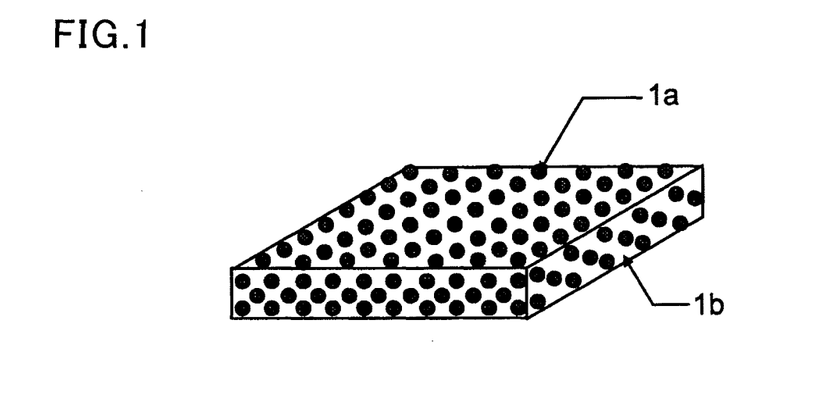
FIG. 1 is a schematic view illustrating an aspect of the oral film-form base and preparation according to the present invention.

The oral film-form base according to the present invention contains one or two or more edible polymers soluble in water and an organic solvent having a solubility parameter of 9.7 or higher, and particles of one or two or more compounds selected from the group consisting of mono- to hexasaccharide sugars and sugar alcohols thereof, having an average particle size of 0.1 μm to 60 μm. FIG. 1 is a view schematically illustrating an aspect of such a base in which particles (1a) of one or two or more compounds of the sugars and sugar alcohols are uniformly dispersed in a film (1b) that contains the edible polymer(s). In the case of the oral film-form preparation according to the present invention, the particles (1a) of one or two or more compounds of sugars and sugar alcohols are uniformly dispersed in the film (1b) that contains the edible polymer(s) and a drug.

The edible polymer soluble in both water and an organic solvent having a solubility parameter of 9.7 or higher in the present invention is not particularly limited as long as the polymer is capable of forming a film, edible, and soluble in the organic solvent in which sugars and sugar alcohols are insoluble. In the present invention, the term "edible" refers to a pharmaceutically acceptable polymer that can be administered orally.

More specifically, the edible polymer is preferably polyvinylpyrrolidone (hereinafter, PVP) and hydroxypropyl cellulose (hereinafter, HPC) because they exhibit sufficient solubility in water and an organic solvent having a solubility parameter of 9.7 or higher, dissolve rapidly in the mouth, and enable use of the above organic solvent in production. Among these, HPC is more preferable because it has less hygroscopicity with regard to relative humidity than PVP, and is considered preferable from a practical standpoint.

Preferably, the weight-average molecular weight of the above PVP used as the edible polymer of the present invention is 2,500 to 3,000,000, and more preferably 2,500 to 1,200,000. If the weight-average molecular weight is less than 2,500, the stability and hygroscopicity of the base and the preparation to be obtained may be adversely affected. In contrast, if the molecular weight exceeds 3,000,000, the solubility in an organic solvent having a solubility parameter of 9.7 or higher may be poor.

Preferably, the weight-average molecular weight of the above HPC used as the edible polymer of the present invention is 10,000 to 1,200,000, and more preferably 10,000 to 370,000. If the weight-average molecular weight is less than 10,000, the stability and hygroscopicity of the base and the preparation to be obtained may be adversely affected. In contrast, if the molecular weight exceeds 1,200,000, the solubility in an organic solvent having a solubility parameter of 9.7 or higher may be poor.

The weight-average molecular weights of the PVP and the HPC are obtained by gel permeation chromatography analysis.

Preferably, the hydroxypropoxy substitution degree in the above HPC used as the edible polymer of the present invention is 50% to 100%. Here, the hydroxypropoxy substitution degree is a value determined in accordance with the quantitative method described in the section entitled "Hydroxypropyl cellulose" in the Official Monographs of the Fifteenth Edition of the Japanese Pharmacopoeia. More preferably, the hydroxypropoxy substitution degree in the above HPC is at least 53.4%. If the hydroxypropoxy substitution degree is less than 53.4%, the solubility of the HPC in water and an organic solvent having a solubility parameter of 9.7 or higher may be poor. The maximum hydroxypropoxy substitution degree in the HPC used in the present invention is preferably about 77.5% as defined in the Official Monographs of the Fifteenth Edition of the Japanese Pharmacopoeia.

Each of these edible polymers may be used alone, or two or more of the edible polymers may be used in combination. Commercially available edible polymers that are provided as pharmaceutical ones may be used as the edible polymer, for convenience. The proportion of the one or two or more edible polymers in the total amount of the oral film-form base or preparation according to the present invention is suitably 10 wt % to 80 wt %, and preferably 20 wt % to 70 wt %. If the proportion of the edible polymer is less than 10 wt %, the film may be fragile and show insufficient strength; in contrast, if the proportion exceeds 80 wt %, the polymer tends to cause a sticky sensation in the mouth.

The edible polymer soluble in both water and an organic solvent having a solubility parameter of 9.7 or higher may be combined with an appropriate amount of an edible polymer soluble only in water or an edible polymer insoluble in water and an organic solvent. Examples of such edible polymers include polymers obtained from natural substances such as acacia gum, gum arabic, sodium alginate, casein, xanthan gum, guar gum, dextran, tragacanth gum, starch, pullulan, and pectin; semisynthetic polymers such as crystalline cellulose, methylcellulose, ethylcellulose, carboxymethylcellulose, carboxymethylcellulose sodium, carboxymethylcellulose calcium, sodium carboxymethyl starch, hydroxyethylcellulose, hydroxypropylmethylcellulose, and low-substituted hydroxypropyl cellulose; and synthetic polymers such as polyvinyl alcohol and a carboxyvinyl polymer. These polymers may be commercially available ones provided as pharmaceutical products.

In the present invention, the following mono- to hexasaccharide sugars and sugar alcohols thereof are used as well as the edible polymer soluble in both water and an organic solvent having a solubility parameter of 9.7 or higher.

Examples of monosaccharides include: aldotetroses such as erythrose and threose; aldopentoses such as ribose, lyxose, xylose, and arabinose; aldohexoses such as allose, talose, gulose, glucose, altrose, mannose, galactose, and idose; ketotetroses such as erythrulose; ketopentoses such as xylulose and ribulose; and ketohexoses such as psicose, fructose, sorbose, and tagatose. Examples of disaccharides include: α-diglucosides such as trehalose, kojibiose, nigerose, maltose, and isomaltose; β-diglucosides such as isotrehalose, sophorose, laminaribiose, cellobiose, and gentiobiose; α,β-diglucocides such as neotrehalose; lactose; sucrose; and isomaltulose (palatinose). An example of trisaccharides is raffinose.

Examples of tri- to hexasaccharide oligosaccharides include cyclic oligosaccharides such as fructooligosaccharides, galactooligosaccharides, xylooligosaccharides, isomaltooligosaccharides, chitin oligosaccharides, chitosan oligosaccharides, oligoglucosamine, and cyclodextrins.

Examples of monosaccharide alcohols include: tetritols such as erythritol, D-threitol, and L-threitol; pentitols such as D-arabinitol and xylitol; hexitols such as D-iditol, galactitol (dulcitol), D-glucitol (sorbitol), and mannitol; and cyclitols such as inositol. Examples of disaccharide alcohols include maltitol, lactitol, and reduced palatinose (isomalt); and examples of oligosaccharides include pentaerythritol and reduced malt sugar starch syrup.

Among these, mono- to trisaccharides and sugar alcohols thereof are preferable from the standpoint of the ease of dissolution in the mouth of the film-form base and preparation. More specifically, lactose, erythritol, xylitol, mannitol, and reduced palatinose (isomalt) which have low hygroscopicity are more preferable. In the present invention, one or two or more compounds selected from the above mono- to hexasaccharide sugars and sugar alcohols thereof are used.

In the present invention, the one or two or more compounds selected from the above mono- to hexasaccharide sugars and sugar alcohols thereof should include particles having an average particle size of 0.1 μm to 60 μm. Preferably, 30 wt % to 80 wt % of the above sugars and sugar alcohols, relative to the total amount of the sugars and sugar alcohols in the base or preparation, are particles having an average particle size in the above range. If the average particle size of one or two or more compounds selected from sugars and sugar alcohols is smaller than 0.1 μm, the respective particles can aggregate, and the flexibility of the film-form base or preparation may be different in some places. Similarly, if particles having an average particle size exceeding 60 μm are contained in a film-form base or preparation of practical thickness, the flexibility of the preparation may be different in some places. The one or two or more compounds selected from sugars and sugar alcohols are more preferably ones including particles having an average particle size of 0.1 μm to 30 μm.

Here, the average particle size of the particles of one or more compounds selected from sugars and sugar alcohols refers to a 50 vol % average particle size determined by a laser-scattering particle size distribution analyzer.

Namely, 10 mg of particles of the sugars or sugar alcohols are added in 3 mL of a chloroform solution of 0.2 wt % polyoxyethylene monolauric acid ester, and the particles are sufficiently dispersed by sonication. The resulting dispersion is added to chloroform so that the transmittance becomes 75% to 85% in a laser-scattering particle size distribution analyzer (LA-950, product of Horiba Ltd.). Then, the 50 vol % average particle size is measured by the wet method.

The particles of one or two or more compounds selected from mono- to hexasaccharide sugars and sugar alcohols thereof preferably constitute 1 wt % to 80 wt %, more preferably 10 wt % to 60 wt %, of the total weight of the base or preparation. In a base or preparation of practical thickness, if the amount of the particles of one or two or more compounds selected from sugars and sugar alcohols is less than 1 wt %, sufficient improvement is not seen in the properties of dissolution profile in the mouth, film strength, a sticky sensation attributed to water-soluble polymers in the mouth, and a feel when handled with the fingers. An amount exceeding 80 wt % may deteriorate the shape retention properties and the like of the base or preparation, unless the average particle size of the sugar and sugar alcohol particles is significantly reduced. As the foregoing sugars and the sugar alcohols, a commercially available product provided for pharmaceutical use is conveniently utilized. Also, a commercially available product can be used after sizing so that the average particle size lies within the above range. Adjustment of the above average particle size can be carried out by methods such as pulverization, granulation through dry granulation, wet granulation or the like, and classification using a sieve, a mechanical classifier or the like.

The solubility of the edible polymer, sugars, and sugar alcohols used in the present invention in water or an organic solvent having a solubility parameter of 9.7 or higher is described by the following terms. That is, if an amount of 100 mL or more of the organic solvent or water is necessary to dissolve 1 g of a solute at 20° C., then the solute is "insoluble". In contrast, if an amount of less than 5 mL of the organic solvent or water is necessary to dissolve 1 g of a solute at 20° C., then the solute is "soluble". When an amount of less than 3 mL of water or the organic solvent is necessary, then the solute is "easily soluble". The sugars and sugar alcohols used in the present invention are known to have low solubility in the organic solvent, and have lower solubility as the temperature of the organic solvent increases. Hence, by increasing the temperature of the organic solvent to lower the solubility of the sugars and sugar alcohols, it is possible to stabilize the sugars and sugar alcohols in the state of particles.

The oral film-form base and preparation according to the present invention may optionally contain a suitable amount of additive (s) such as a plasticizer (e.g., polyethylene glycol), a surfactant, a stabilizer, a preservative, an antioxidant, a fragrance, a flavor, a sweetener, and a colorant, as well as the edible polymer and the one or two or more compounds selected from the group constituting of sugars and sugar alcohols.

The drug to be contained in the oral film-form preparation according to the present invention is not particularly limited as long as it can be orally administrated. Examples thereof include antineoplastics, antiinflammatory drugs, antiallergic drugs, antidiabetic drugs, antihyperlipidemic drugs, bone/calcium metabolic drugs, antihypertensive drugs, antianginal drugs, antiarrhythmic drugs, vasodilator drugs, diuretics, bronchodilators, antiasthmatic drugs, antitussives, expectorant drugs, digestants, gastrointestinal function regulators, anti-peptic ulcer drugs, drugs for bowel disease, laxatives, antipsychotics, antidepressants, mood stabilizers, psychostimulants, hypnotics, antianxiety drugs, antiepileptics, drugs for migraine, antiemetics, antidinics, antiparkinson drugs, cerebral ameliorators, antidementia drugs, antibacterial drugs, antiviral drugs, antifungal drugs, drugs for frequent urination and voiding disorders, and drugs for urinary incontinence. The amount of a drug to be contained in a preparation will differ depending on the kind and titer of the drug and the symptoms of the patient to take the preparation, and the like. Still, in consideration of the required dosage, the amount is commonly 0.1 wt % to 60 wt % of the total amount of the preparation.

Specific examples of the drugs include zolmitriptan, diphenhydramine, tamuslosin, granisetron, torterosin, scopolamine, famotidine, candesartan cilexetil, pioglitazone, amlodipine, donepezil, and salts thereof.

The drug used in the present invention preferably does not taste bitter because the film-form preparation according to the present invention is to be administrated orally, but drugs that do taste bitter can also be suitably used by performing a bitterness masking technique, for example, microencapsulation, or by adding a bitterness blocking agent, sweetener, flavoring, or fragrance. Many of the sugars and sugar alcohols used in the present invention give sweetness, and can be expected to provide a drug-bitterness masking effect.

The thickness of the film-form base and preparation according to the present invention is not particularly limited herein, but is preferably 30 μm to 300 μm. If the thickness is smaller than 30 μm, the film strength may decrease and thus the handling properties of the preparation may deteriorate. If the thickness exceeds 300 μm, the preparation may require more time to dissolve in the mouth, thereby not dissolving easily. The planar shape of the film-form base and preparation of the present invention may be a common shape such as a rectangle, a square, a circle, and an ellipse.

The oral film-form base according to the present invention can be produced by dissolving or dispersing, in an organic solvent having a solubility parameter of 9.7 or higher, one or two or more edible polymers soluble in water and the organic solvent, and particles of one or two or more compounds selected from the group consisting of mono- to hexasaccharide sugars and sugar alcohols thereof, having an average particle size of 0.1 μm to 60 μm, and forming a thin layer of the resulting dispersion and then drying the layer. Similarly to the base, an oral film-form preparation can be produced by dissolving or dispersing, in an organic solvent having a solubility parameter of 9.7 or higher, a drug, one or two or more edible polymers soluble in water and the organic solvent, and particles of one or two or more compounds selected from the group consisting of mono- to hexasaccharide sugars and sugar alcohols thereof, having an average particle size of 0.1 μm to 60 μm, and forming a thin layer of the resulting dispersion, and then drying the layer.

More preferably, an oral film-form base is produced through the following processes. Firstly, a predetermined amount of an edible polymer is dissolved in a portion of an organic solvent which has a solubility parameter of 9.7 or higher and in which the polymer is soluble. Separately, particles of one or two or more compounds selected from the group consisting of sugars and sugar alcohols are subjected to processes such as pulverization, granulation, and classification to adjust the average particle size thereof, and then the particles are uniformly dispersed in the rest of the organic solvent. The dispersion and other additive (s) such as a plasticizer as needed are mixed with the solution of the edible polymer in the organic solvent. An appropriate amount of the mixture is spread onto a release film made of polystyrene or polyethylene terephthalate, and is then dried. Thereby, a film-form base is produced. The amount of the above organic solvent to dissolve the edible polymer is preferably 1 to 2 times the weight of the edible polymer. In the case of producing an oral film-form preparation, a solution is prepared by dissolving an edible polymer in a portion of an organic solvent having a solubility parameter of 9.7 or higher. A drug is dissolved or dispersed in the rest of the organic solvent, and particles of one or two or more compounds selected from sugars and sugar alcohols are then dispersed in the solvent. To the dispersion are added the solution of the edible polymer and other additive(s) such as a plasticizer according to need. In the similar manner as described above, an appropriate amount of the mixture is spread onto a release film, and is then dried. The dried product is cut into desired shapes of a desired size, and seal-packaged as needed. Thereby, an oral film-form preparation is produced.

The organic solvent having a solubility parameter of 9.7 or higher which is used in production of the oral film-form preparation according to the present invention may be one in which sugars or sugar alcohols are insoluble but an edible polymer is soluble. Examples thereof include methanol, ethanol, isopropanol, propylene glycol, methylene chloride, and acetone. Any one of the compounds selected from these may be used alone, or two or more of the compounds may be used in combination. Among these, lower alcohols such as methanol, ethanol, and isopropanol, methylene chloride, and acetone are preferable, and purified water can also be added if the amount thereof is small. If the solution bubbles during the course of preparation thereof, the solution is to be deaerated by leaving the solution to stand overnight or by vacuum deaeration.

In the present description, the term "solubility parameter" (SP value) refers to the square root of the heat of evaporation (cal/cm$^3$) required for one mole by volume of the liquid to evaporate. Table 1 shows the solubility parameter of organic solvents and water which can be used in the present invention. The solubility parameter of the organic solvent which can be used in the present invention is preferably 9.7 to 20, and more preferably 9.7 to 15. A solvent having a solubility parameter exceeding 20 is not preferable for the purpose of the present invention because it may possibly dissolve sugars or sugar alcohols.

TABLE 1

| Solvent | Solubility parameter (SP value) |
| --- | --- |
| Methanol | 14.5 to 14.8 |
| Ethanol | 12.7 |
| Isopropanol | 11.5 |
| Propylene glycol | 14.3 |
| Methylene chloride | 9.7 |
| Acetone | 10.0 |
| Water | 23.4 |

EXAMPLES

The present invention will be more specifically described by means of the following Examples which, however, are not intended to limit the scope of the present invention.

The particles of sugars and sugar alcohols used in Examples and Comparative Examples were pulverized, subjected to screening with a sieve (32 μm, 50 μm, or 90 μm), and measured for the 50 volt average particle size with a laser-scattering particle size distribution analyzer. The resulting value was used as the particle size index of the respective particles. Table 2 shows the 50 vol % average particle sizes of the particles of sugars and sugar alcohols used.

TABLE 2

| Sugars and Sugar alcohols | 50 vol % average particle size [μm] |
| --- | --- |
| D-mannitol fine particles | 15 |
| D-mannitol fine particles A | 11 |
| D-mannitol fine particles B | 33 |
| D-mannitol fine particles C | 55 |
| Lactose fine particles | 8 |
| Maltose fine particles | 13 |
| Xylitol fine particles | 21 |
| Glucose fine particles | 11 |
| Isomalt fine particles | 12 |
| Erythritol fine particles | 15 |
| Raffinose fine particles | 12 |
| Oligoglucosamine fine particles | 17 |

Examples 1, 2

Table 3 shows the formulations of the oral film-form preparations in Examples 1 and 2 in the present invention, and the formulations in Comparative Examples 1 and 2.

TABLE 3

| | Examples (parts by weight) | | Comparative Examples (parts by weight) | |
| --- | --- | --- | --- | --- |
| Component | 1 | 2 | 1 | 2 |
| Zolmitriptan | 9.0 | 9.0 | 9.0 | 9.0 |
| HPC | 47.0 | — | — | — |
| PVP K-30 | — | 47.0 | — | — |
| Pullulan | — | — | 47.0 | — |
| Hydroxypropylmethyl cellulose | — | — | — | 47.0 |
| Polyethylene glycol 400 | 4.0 | 4.0 | 4.0 | 4.0 |
| D-mannitol fine particles | 40.0 | 40.0 | 40.0 | 40.0 |
| Purified water | — | — | 183.3 | 200.0 |
| Ethanol | 120.5 | 137.2 | 33.3 | 33.3 |

The oral film-form preparations in Examples 1 and 2 were produced through the following processes. According to Table 3, 47.0 parts by weight of HPC (weight-average molecular weight=about 30,000, hydroxypropoxy substitution degree=53.4 to 77.5%) or PVP K-30 (weight-average molecular weight=about 40,000) was dissolved in 70.5 parts by weight of ethanol through stirring, to prepare an ethanol solution of HPC or PVP K-30. In the rest of ethanol, 9.0 parts by weight of zolmitriptan was dissolved through stirring, and then 40.0 parts by weight of D-mannitol fine particles, having been subjected to screening with a 32-μm sieve in advance, were dispersed through ultrasonic agitation. The dispersion was mixed with the ethanol solution of HPC or PVP K-30 and 4.0 parts by weight of polyethylene glycol through stirring, and the mixture was sufficiently deaerated. The mixture was spread onto a release film made of polyethylene terephthalate, and was then dried. Thereby, a film having a thickness of about 100 μm was produced. The obtained film was cut into 3-cm$^2$ rectangles, whereby a film-form preparation was produced.

The oral film-form preparations in Comparative Examples 1 and 2 were produced through the following processes. According to Table 3, 9.0 parts by weight of zolmitriptan was heat-dissolved in 33.3 parts by weight of ethanol. An amount of 47.0 parts by weight of pullulan or hydroxypropyl methylcellulose, 4.0 parts by weight of polyethylene glycol, and 40.0 parts by weight of D-mannitol fine particles, having been subjected to screening with a 32-μm sieve in advance, were dissolved in purified water through stirring. The ethanol solution of zolmitriptan was dissolved in the dispersion through stirring at 45° C. The resulting solution was sufficiently deaerated, spread onto a release film made of polyethylene terephthalate, and then dried, whereby a film having a thickness of about 100 μm was produced. The obtained film was cut into 3-cm² rectangles, and thereby a film-form preparation was produced.

Examples 3 to 10

Table 4 shows the formulations of the oral film-form preparations in Examples 3 to 10 in the present invention. The preparations were produced by the same procedure as that for the oral film-form preparations in Examples 1 and 2. Namely, zolmitriptan was dissolved in ethanol, and fine particles of sugars or sugar alcohols, having been subjected to screening with a 32-μm sieve in advance, were dispersed therein. Subsequently, a solution prepared by adding HPC to 70.5 parts by weight of ethanol, and polyethylene glycol were mixed with the dispersion. The mixture was sufficiently deaerated, spread onto a release film made of polyethylene terephthalate, and then dried. Thereby, a film having a thickness of about 100 μm was produced. The film was cut into 3-cm² rectangles, whereby an oral film-form preparation was produced.

TABLE 4

| Component | Examples (parts by weight) | | | | | | | |
|---|---|---|---|---|---|---|---|---|
| | 3 | 4 | 5 | 6 | 7 | 8 | 9 | 10 |
| Zolmitriptan | 9.0 | 9.0 | 9.0 | 9.0 | 9.0 | 9.0 | 9.0 | 9.0 |
| HPC | 47.0 | 47.0 | 47.0 | 47.0 | 47.0 | 47.0 | 47.0 | 47.0 |
| Polyethylene glycol 400 | 4.0 | 4.0 | 4.0 | 4.0 | 4.0 | 4.0 | 4.0 | 4.0 |
| Lactose fine particles | 40.0 | — | — | — | — | — | — | — |
| Maltose fine particles | — | 40.0 | — | — | — | — | — | — |
| Isomalt fine particles | — | — | 40.0 | — | — | — | — | — |
| Xylitol fine particles | — | — | — | 40.0 | — | — | — | — |
| Erythritol fine particles | — | — | — | — | 40.0 | — | — | — |
| Glucose fine particles | — | — | — | — | — | 40.0 | — | — |
| Raffinose fine particles | — | — | — | — | — | — | 40.0 | — |
| Oligoglucosamine fine particles | — | — | — | — | — | — | — | 40.0 |
| Ethanol | 137.2 | 137.2 | 137.2 | 120.5 | 137.2 | 103.8 | 153.8 | 103.8 |

Comparative Examples 3 to 13

Table 5 shows the formulations in Comparative Examples 3 to 13.

TABLE 5

| Component | Comparative Examples (parts by weight) | | | | | | | | | | |
|---|---|---|---|---|---|---|---|---|---|---|---|
| | 3 | 4 | 5 | 6 | 7 | 8 | 9 | 10 | 11 | 12 | 13 |
| Zolmitriptan | 9.0 | 9.0 | 9.0 | 9.0 | 9.0 | 9.0 | 9.0 | 9.0 | 9.0 | 9.0 | 9.0 |
| HPC | 87.0 | 47.0 | 47.0 | 47.0 | 47.0 | 47.0 | 47.0 | 47.0 | 47.0 | 47.0 | 87.0 |
| Polyethylene glycol 400 | 4.0 | 4.0 | 4.0 | 4.0 | 4.0 | 4.0 | 4.0 | 4.0 | 4.0 | 4.0 | 4.0 |
| D-mannitol fine particles | — | 40.0 | — | — | — | — | — | — | — | — | — |
| Lactose fine particles | — | — | 40.0 | — | — | — | — | — | — | — | — |
| Maltose fine particles | — | — | — | 40.0 | — | — | — | — | — | — | — |
| Isomalt fine particles | — | — | — | — | 40.0 | — | — | — | — | — | — |
| Xylitol fine particles | — | — | — | — | — | 40.0 | — | — | — | — | — |
| Erythritol fine particles | — | — | — | — | — | — | 40.0 | — | — | — | — |
| Glucose fine particles | — | — | — | — | — | — | — | 40.0 | — | — | — |
| Raffinose fine particles | — | — | — | — | — | — | — | — | 40.0 | — | — |
| Oligoglucosamine fine particles | — | — | — | — | — | — | — | — | — | 40.0 | — |
| Ethanol | 116.7 | 33.3 | 33.3 | 33.3 | 33.3 | 33.3 | 33.3 | 33.3 | 33.3 | 33.3 | 33.3 |
| Purified water | — | 170.6 | 170.6 | 137.3 | 137.3 | 137.3 | 137.3 | 137.3 | 137.3 | 137.3 | 137.3 |

The oral film-form preparation in Comparative Example 3 was produced by the same procedure as that for the film-form preparation in Example 1, except that, in accordance with Table 5, zolmitriptan and polyethylene glycol were dissolved in ethanol to prepare a dispersion, and the ethanol solution of HPC was added to the dispersion.

The oral film-form preparations in Comparative Examples 4 to 13 were produced through the following processes. Firstly, zolmitriptan was heat-dissolved in ethanol. HPC (weight-average molecular weight=about 30,000, hydroxypropoxy substitution degree=53.4 to 77.5%), polyethylene glycol, and fine particles of sugars or sugar alcohols, having been subjected to screening with a 32-μm sieve in advance, were dissolved in purified water through stirring. The ethanol solution of zolmitriptan was dissolved in the dispersion through stirring at 45° C. The resulting mixture was sufficiently deaerated, spread onto a release film made of polyethylene terephthalate, and then dried.

The thus produced films in Comparative Examples 3 to 13 except for Comparative Examples 3, 5, 7, 12, and 13 were very fragile and soft and therefore the films were not able to be peeled off the release film made of polyethylene terephthalate. For this reason, no film-form preparation was obtained in those Comparative Examples. Each of the films obtained in Comparative Examples 3, 5, 7, 12, and 13 was cut into 3-cm$^2$ rectangles so that a film-form preparation was obtained.

Examples 11 to 20

Table 6 shows the formulations of the oral film-form preparations in Examples 11 to 20 according to the present invention.

TABLE 6

| Component | Examples (parts by weight) | | | | | | | | | |
|---|---|---|---|---|---|---|---|---|---|---|
| | 11 | 12 | 13 | 14 | 15 | 16 | 17 | 18 | 19 | 20 |
| Diphenhydramine hydrochloride | 50.0 | — | — | — | — | — | — | — | — | — |
| Tamsulosin hydrochloride | — | 0.7 | — | — | — | — | — | — | — | — |
| Granisetron hydrochloride | — | — | 10.0 | — | — | — | — | — | — | — |
| Tolterodine tartrate | — | — | — | 13.3 | — | — | — | — | — | — |
| Scopolamine hydrobromide | — | — | — | — | 0.8 | — | — | — | — | — |
| Famotidine | — | — | — | — | — | 25.0 | — | — | — | — |
| Candesartan cilexetil | — | — | — | — | — | — | 10.0 | — | — | — |
| Pioglitazone hydrochloride | — | — | — | — | — | — | — | 41.6 | — | — |
| Amlodipine besilate | — | — | — | — | — | — | — | — | 12.4 | — |
| Donepezil hydrochloride | — | — | — | — | — | — | — | — | — | 14.9 |
| HPC | 36.0 | 40.3 | 36.0 | 37.7 | 40.2 | 36.0 | 40.0 | 38.0 | 39.0 | 38.0 |
| Polyethylene glycol 400 | 4.0 | 4.0 | 4.0 | 4.0 | 4.0 | 4.0 | 4.0 | 4.0 | 4.0 | 4.0 |
| D-mannitol fine particles | 10.0 | 55.0 | 50.0 | 45.0 | 55.0 | 35.0 | 46.0 | 16.4 | 44.6 | 43.1 |
| Ethanol | 140.0 | 184.1 | 173.3 | 152.6 | 180.5 | 160.0 | 122.2 | 122.2 | 122.2 | 122.2 |

The oral film-form preparations in Examples 11 to 16 were produced through the following processes. That is, as shown in Table 6, HPC (weight-average molecular weight=about 30,000, hydroxypropoxy substitution degree=53.4 to 77.5%) was dissolved through stirring in ethanol in an amount 1.5 times the weight of HPC, so that an ethanol solution of HPC was produced. A drug was dissolved in the rest of ethanol through stirring, and this solution was mixed, through stirring, with D-mannitol fine particles, the ethanol solution of HPC, and polyethylene glycol. The mixture was spread onto a release film made of polyethylene terephthalate, and then dried. Thereby, a film having a thickness of about 100 μm was produced. The obtained film was cut into 3-cm$^2$ rectangles, whereby a film-form preparation was produced.

The oral film-form preparations in Examples 17 to 20 were produced through the following processes. That is, as shown in Table 6, a drug, D-mannitol fine particles, and polyethylene glycol were dispersed in ethanol through 10-minute sonication. In the dispersion, HPC (weight-average molecular weight=about 30,000, hydroxypropoxy substitution degree=53.4 to 77.5%) was dissolved. The resulting solution was spread onto a release film made of polyethylene terephthalate, and then dried. Thereby, a film having a thickness of about 70 μm was produced. The obtained film was cut into 3-cm$^2$ rectangles, whereby a film-form preparation was produced.

Examples 21 to 26

Table 7 shows the formulations of the oral film-form bases in Examples 21 to 26 according to the present invention.

TABLE 7

| Component | Examples (parts by weight) | | | | | |
|---|---|---|---|---|---|---|
| | 21 | 22 | 23 | 24 | 25 | 26 |
| HPC | 46.0 | 46.0 | 46.0 | 91.0 | 71.0 | 21.0 |
| Polyethylene glycol 400 | 4.0 | 4.0 | 4.0 | 4.0 | 4.0 | 4.0 |
| D-mannitol fine particles A | 50.0 | — | — | 5.0 | 25.0 | 75.0 |
| D-mannitol fine particles B | — | 50.0 | — | — | — | — |
| D-mannitol fine particles C | — | — | 50.0 | — | — | — |
| Ethanol | 120.0 | 120.0 | 120.0 | 121.0 | 137.0 | 98.4 |

These bases were prepared as described below. That is, as shown in Table 7, HPC (weight-average molecular weight=about 30,000, hydroxypropoxy substitution degree=53.4 to 77.5%) was dissolved through stirring in ethanol in an amount 1.5 times the weight of HPC (Examples 21 to 23 and 26) or in an amount 1.0 times the weight of HPC (Examples 24 and 25), so that an ethanol solution of HPC was produced. D-mannitol fine particles were dispersed in the rest of ethanol through sonication. The dispersion was then mixed with the ethanol solution of HPC and polyethylene glycol. The mixture was spread onto a release film made of polyethylene terephthalate, and then dried. Thereby, a film having a thickness of about 100 μm was produced. The obtained film was cut into 3-cm$^2$ rectangles, whereby a film-form base was produced.

The oral film-form preparations and bases prepared in the Examples and Comparative Examples according to the present invention were evaluated for film strength, a sticky sensation in the mouth, dissolution profile in the mouth, and a feel when touched with the fingers, through measurements by release properties test, stiffness test, tensile strength test, tack duration test, oral dissolution test, and sensory test (feel). The average particle size of the fine particles of sugars and sugar alcohols dispersed in each film-form base was determined using a microscope. Each test method is described below.

(1) Peel Properties Test

Each sample of the film-form preparations or bases was peeled off the polyethylene terephthalate film during production thereof, and was given a score using the following criteria.

[Evaluation Criteria]
4: Can be peeled off easily
3: Can be peeled off
2: Can be peeled off with some effort
1: Can be peeled off with effort, but film tears
0: Cannot be peeled off at all (2) Stiffness Test This test was performed following the test method of "JIS L1096 Testing Methods for Woven Fabrics, 8.19 Stiffness, 8.19.1 Method A (45° cantilever method)". In this test, five 20 mm×150 mm test pieces were selected from the sample of each of the Examples and Comparative Examples, and the short dimension of the test piece was aligned with the baseline of the scale on a smooth-surfaced, flat platform with one end having a 45° downward slope. Next, the test piece was gently slid in the direction of the slope by a suitable method, and when the center point of an edge of the test piece came into contact with the slope A, the position of the trailing edge was read on the scale. Stiffness is expressed as the length (mm) that the test piece was moved. Stiffness was determined by measuring the moved distances of the five test pieces both face up and face down both forward and backward, and then calculating the mean value. The evaluation criteria were based on the stiffness (about 60 mm) of the film-form preparation containing no sugar therein (Comparative Example 3), and are listed below. If the prepared sample could not be physically peeled off the release film and thus could not give a film-form preparation, the sample was given a score of 0.

[Evaluation Criteria]
4: 60±10 mm or more, less than 60±20 mm
3: 60±20 mm or more, less than 60±30 mm
2: 60±30 mm or more, less than 60±40 mm
1: 60±40 mm or more (3) Tensile Strength Test This test was carried out following "JIS K7127 Testing Method for Tensile Properties of Plastic Films and Sheets". Each of the film-form bases and preparations was cut to a 12 mm×50 mm test sample, and the test was performed thereon after thorough drying in a desiccator. A small, tabletop vertical tensile test apparatus (produced by Shimadzu Corporation, EZ TEST-100M) was used to perform the test at a draw rate of 60 mm/min. Because almost no stretching was seen in the test samples, the tensile strength at the measured yield point was used as the tensile strength value. The test was repeated three times for each sample, and the mean value was recorded as the tensile strength. The tensile strength was then converted into a score using the following criteria. If the prepared sample could not be physically peeled off the release film and thus could not give a film-form preparation, the sample was given a score of 0.

Figure 2:
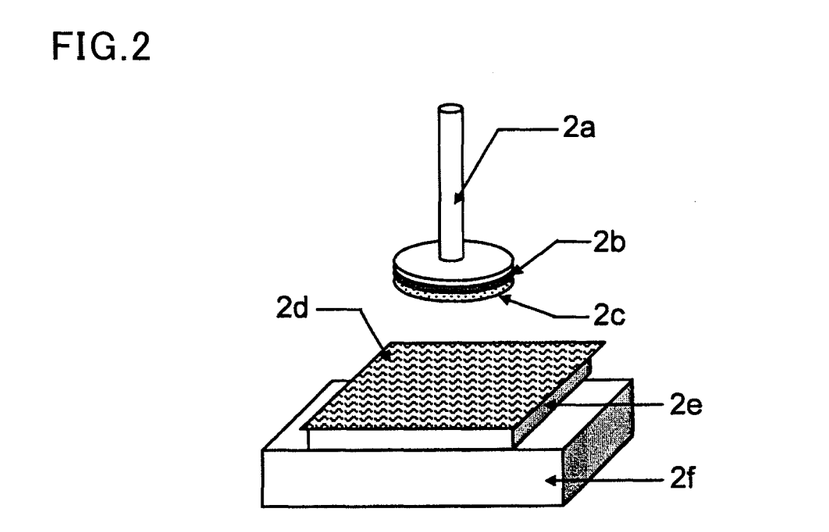
FIG. 2 is a schematic view illustrating measurement of tack duration.

[Evaluation Criteria]
4: Tensile strength=10 N or more, less than 20 N
3: Tensile strength=5 N or more, less than 10 N
2: Tensile strength=2 N or more, less than 5 N
1: Tensile strength=less than 2 N (4) Tack Duration Test The test was performed using a rheometer (SUN SCIENTIFIC, CR-2000) with a 12-mm diameter test piece cut out from each of the film-form preparations and bases. Here, "tack" refers to the adhesion strength of the test piece to an adherend at the time of bringing, by a weak force, the test piece into contact with the adherend for a short time. The test environment is shown in FIG. 2. First, the test piece 2c was adhered to a 12-mm diameter probe 2a with double-sided tape 2b. Separately, a piece of rubber 2e was mounted on a test platform 2f, and a collagen film 2d soaked with water was placed thereon. Then 200 µL of purified water was applied to the test piece, and the probe 2a with the test piece 2c adhered thereto was lowered, placed in contact with the top of the collagen film 2d, and then raised. At that time, the tack duration after the initial tack, which was obtained when the probe 2a was released from the collagen film 2d, was measured on recording paper using a slide caliper. The measured results were converted into scores using the following criteria. The samples evaluated as being unable to be peeled off at all were cut together with the release film, and the release film side was adhered to the probe with double-sided tape. Then, the tack duration was measured in the same manner.

[Evaluation Criteria]
4: Tack duration time measurement value=less than 2 mm
3: Tack duration time measurement value=2 or more, less than 3 mm
2: Tack duration time measurement value=3 or more, less than 4 mm
1: Tack duration time measurement value=4 mm or more (5) Oral Dissolution Test First, 900 mL of a pH 6.8 phosphate buffer was placed in a 1000-mL low glass petri dish, a stainless steel mesh basket (Φ4 mm) was inverted and submerged therein, and agitation was provided by a stirrer (300 rpm). The temperature of the liquid was maintained at 37±2° C. using a constant temperature water circulator. A test piece (3 cm$^2$) was submerged, and concurrently a 3 cm×3 cm stainless steel screen (5 mm mesh) was placed on top as a sinker. The disintegration of the test piece was checked visually, and the duration from the time the test piece was submerged until the test piece had finished disintegrating was measured with a stopwatch. The measurement of each sample was repeated three times, and the mean value thereof was used as the oral dissolution time. The oral dissolution time was converted into a score using the following criteria. If the prepared sample could not be physically peeled off the release film and thus could not give a film-form preparation, the sample was given a score of 0.

[Evaluation Criteria]
4: Oral dissolution time=shorter than 10 sec.
3: Oral dissolution time=10 sec. or longer, shorter than 15 sec.
2: Oral dissolution time=15 sec. or longer, shorter than 20 sec.
1: Oral dissolution time=20 sec. or longer (6) Sensory Test (Feel)

The respective cut film-form preparations or bases were evaluated for an unpleasant sticky sensation by panelist, on the surface by tracing a circle thereon with the fingers for 5 sec., based on the following criteria. If the prepared sample could not be physically peeled off the release film and thus could not give a film-form preparation, the sample was given a score of 0.

[Evaluation Criteria]
4: No sticky sensation
3: Slightly sticky but not unpleasant 2: Unpleasant sticky sensation
1: Very sticky, and film remains on the fingers
(7) Average Particle Size of Fine Particles of Sugar Alcohols in Film-Form Base The particle size of the D-mannitol fine particles A to C in the oral film-form base in each of Examples 21 to 23 according to the present invention was measured using a microscope (product of Keyence Corp., model VHX-600). First, 200 particles were measured, and then the 50 vol % average particle size was calculated therefrom.

Table 8 shows the evaluation results of the tests (1) to (6) performed on the film-form preparations in Examples 1 to 10.

TABLE 8

| Examples | Peel properties | Stiffness | Tensile strength | Tack duration | Oral dissolution | Sensory (feel) | Total |
|---|---|---|---|---|---|---|---|
| 1 | 4 | 4 | 4 | 4 | 4 | 4 | 24 |
| 2 | 4 | 2 | 3 | 4 | 4 | 3 | 20 |
| 3 | 4 | 4 | 4 | 4 | 3 | 4 | 23 |
| 4 | 4 | 4 | 4 | 4 | 4 | 2 | 22 |
| 5 | 4 | 4 | 4 | 4 | 4 | 4 | 24 |
| 6 | 4 | 3 | 3 | 4 | 4 | 4 | 22 |
| 7 | 4 | 4 | 3 | 3 | 4 | 3 | 21 |
| 8 | 4 | 4 | 4 | 4 | 4 | 3 | 23 |
| 9 | 4 | 3 | 3 | 4 | 3 | 3 | 20 |
| 10 | 4 | 3 | 3 | 4 | 4 | 3 | 21 |

All the oral film-form preparations listed in Table 8 received good evaluation scores in the respective tests, except that the oral film-form preparation in Example 4 received a slightly bad evaluation score in the sensory test. That is, Table 8 shows that the oral film-form preparation in each of Examples 1 to 10 of the present invention showed good release properties, had sufficient strength and good oral dissolution, and provided only a slight sticky sensation and a good feel.

Table 9 shows the evaluation results of the tests (1) to (6) performed on the film-form preparations in Comparative Examples 1 to 13.

TABLE 9

| Comparative Examples | Peel properties | Stiffness | Tensile strength | Tack duration | Oral dissolution | Sensory (feel) | Total |
|---|---|---|---|---|---|---|---|
| 1 | 2 | 1 | 1 | 2 | 2 | 2 | 10 |
| 2 | 4 | 2 | 3 | 2 | 3 | 2 | 16 |
| 3 | 3 | 4 | 4 | 1 | 2 | 1 | 15 |
| 4 | 0 | 0 | 0 | 4 | 0 | 0 | 4 |
| 5 | 1 | 0 | 0 | 3 | 0 | 1 | 5 |
| 6 | 0 | 0 | 0 | 3 | 0 | 0 | 3 |
| 7 | 1 | 0 | 0 | 4 | 0 | 1 | 6 |
| 8 | 0 | 0 | 0 | 4 | 0 | 0 | 4 |
| 9 | 0 | 0 | 0 | 2 | 0 | 0 | 2 |
| 10 | 0 | 0 | 0 | 1 | 0 | 0 | 1 |
| 11 | 0 | 0 | 0 | 2 | 0 | 0 | 2 |
| 12 | 1 | 0 | 0 | 4 | 0 | 0 | 5 |
| 13 | 2 | 4 | 4 | 1 | 2 | 1 | 14 |

The oral film-form preparation in Comparative Example 1 in Table 9, produced by dissolving, in purified water, pullulan that is an edible polymer soluble in water but almost insoluble in ethanol, did not receive a good evaluation score in any of the tests. The oral film-form preparation in Comparative Example 2, produced using hydroxypropyl methylcellulose that is an edible polymer soluble in water but almost insoluble in ethanol, had low strength against bending deflection and provided a sticky sensation. The oral film-form preparation in Comparative Example 3 containing no sugars or sugar alcohols had poor oral dissolution and provided a high sticky sensation. Each of the oral film-form preparations in Comparative Examples 4 to 12 produced by dissolving HPC in purified water did not have sufficient strength as a film. The oral film-form preparation in Comparative Example 13, produced by dissolving HPC in purified water without using fine particles of sugars and sugar alcohols, had poor oral dissolution and provided a high sticky sensation.

Table 10 shows the evaluation results of the tests (1) to (6) performed on the film-form preparations in Examples 11 to 20.

TABLE 10

| Examples | Peel properties | Stiffness | Tensile strength | Tack duration | Oral dissolution | Sensory (feel) | Total |
|---|---|---|---|---|---|---|---|
| 11 | 4 | 4 | 2 | 4 | 4 | 4 | 22 |
| 12 | 4 | 4 | 3 | 4 | 3 | 4 | 22 |
| 13 | 4 | 4 | 3 | 4 | 4 | 4 | 23 |
| 14 | 4 | 4 | 2 | 4 | 4 | 4 | 22 |
| 15 | 4 | 4 | 3 | 4 | 4 | 4 | 23 |
| 16 | 4 | 4 | 3 | 4 | 4 | 4 | 23 |
| 17 | 4 | 4 | 3 | 4 | 4 | 4 | 23 |
| 18 | 4 | 4 | 3 | 3 | 3 | 4 | 21 |
| 19 | 4 | 4 | 3 | 4 | 4 | 4 | 23 |
| 20 | 4 | 4 | 3 | 4 | 4 | 4 | 23 |

Each of the oral film-form preparations in Examples 11 to 20 of the present invention listed in Table 10 received good evaluation scores in the respective tests, and had sufficient film strength, good oral dissolution, and a good feel even when containing any of various drugs.

Table 11 shows the evaluation results of the tests (1) to (6) performed on the film-form bases in Examples 21 to 26.

TABLE 11

| Examples | Peel properties | Stiffness | Tensile strength | Tack duration | Oral dissolution | Sensory (feel) | Total |
|---|---|---|---|---|---|---|---|
| 21 | 4 | 4 | 4 | 4 | 4 | 4 | 24 |
| 22 | 4 | 4 | 3 | 4 | 3 | 4 | 22 |
| 23 | 4 | 4 | 2 | 4 | 3 | 4 | 21 |
| 24 | 4 | 3 | 4 | 1 | 4 | 3 | 19 |
| 25 | 4 | 3 | 4 | 3 | 4 | 4 | 22 |
| 26 | 3 | 3 | 1 | 4 | 4 | 4 | 19 |

Each of the oral film-form bases in Examples 21 to 26 of the present invention listed in Table 11 received good evaluation scores in the respective tests except for the tack duration time of the film-form base in Example 24 and the tensile strength of the film-form base in Example 26.

Figure 3:
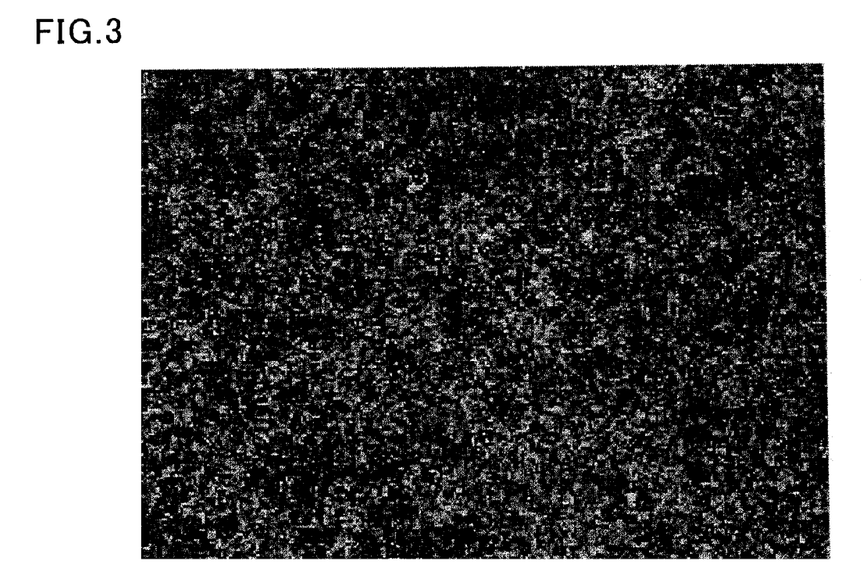
FIG. 3 is a view (magnification: ×1000) showing the surface of an oral film-form base in Example 21 of the present invention.
Figure 4:
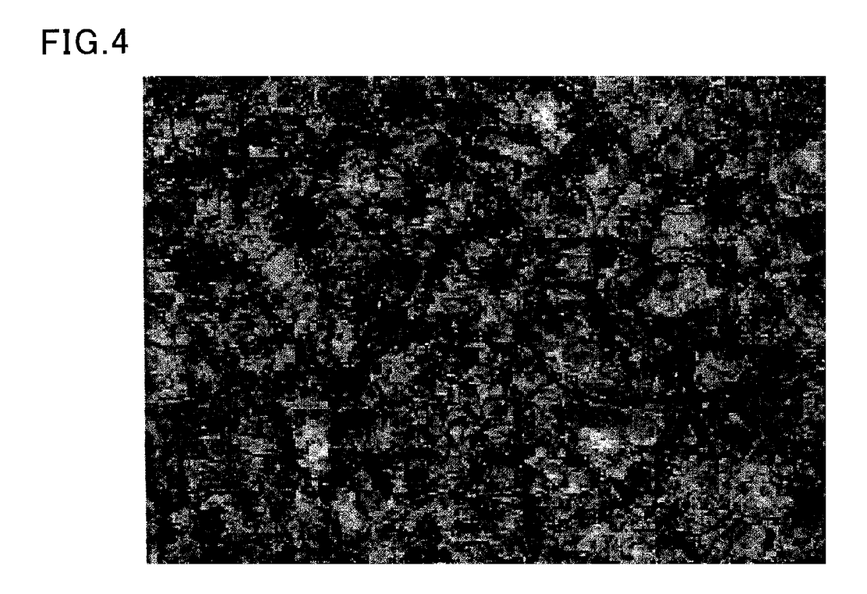
FIG. 4 is a view (magnification: ×1000) showing the surface of an oral film-form base in Example 22 of the present invention.
Figure 5:
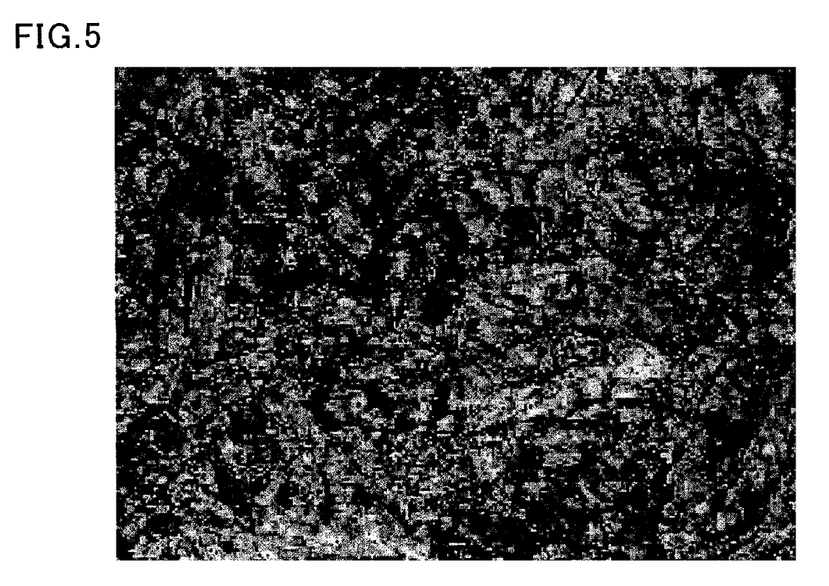
FIG. 5 is a view (magnification: ×500) showing the surface of an oral film-form base in Example 23 of the present invention.

Table 12 shows the results of the average particle size determination for the oral film-form bases in Examples 21 to 23. FIGS. 3 to 5 each show an image taken with a microscope.

TABLE 12

| Examples | 50 vol % average particle size (μm) of D-mannitol fine particles before addition | 50 vol % average particle size (μm) of D-mannitol fine particles in film-form base |
|---|---|---|
| 21 | 11 | 8 |
| 22 | 33 | 28 |
| 23 | 55 | 51 |

Table 12 shows that the 50 vol % average particle size of D-mannitol fine particles did not change much in each of the oral film-form bases in Examples 21 to 23 of the present invention, compared to that before addition, meaning that D-mannitol was dispersed in the base as fine particles without dissolving. Good dispersion of the D-mannitol fine particles was also seen in the observation of the oral film-form bases in Examples 21 to 23 with a microscope, as shown in FIGS. 3 to 5.

INDUSTRIAL APPLICABILITY

The present invention provides oral film-form base and preparation that have sufficient film strength and a rapid dissolution profile in the mouth, and provide a reduced sticky sensation in the mouth and an improved feel when handled with the fingers.

The present application claims priority to the international application PCT/JP2009/051511 filed under the Patent Cooperation Treaty, the entire contents of which are hereby incorporated by reference.

The invention claimed is:

1. An oral film-form base comprising
one or two or more edible, film-forming polymers soluble in water and an organic solvent having a solubility parameter of 9.7 or higher, and
at least one compound selected from the group consisting of mono- to hexasaccharide sugars and sugar alcohols,
wherein the at least one compound is in the form of particles,
the particles are dispersed in the edible, film-forming polymers,
wherein the particles have an average particle size of 0.1 μm to 60 μm, and
wherein the particles are insoluble in the organic solvent having a solubility parameter of 9.7 or higher.

2. The oral film-form base according to claim 1, wherein the particles have an average particle size of 0.1 μm to 30 μm.

3. The oral film-form base according to claim 1, wherein the edible, film-forming polymers soluble in water and an organic solvent having a solubility parameter of 9.7 or higher are one or two or more compounds selected from the group consisting of polyvinylpyrrolidone and hydroxypropyl cellulose.

4. The oral film-form base according to claim 3, wherein polyvinylpyrrolidone has a weight-average molecular weight of 2,500 to 3,000,000.

5. The oral film-form base according to claim 3, wherein hydroxypropyl cellulose has a weight-average molecular weight of 10,000 to 1,200,000.

6. The oral film-form base according to claim 3, wherein hydroxypropyl cellulose has a hydroxypropoxy substitution degree of 50% to 100%.

7. An oral film-form preparation comprising a drug in the oral film-form base according to claim 1.

8. A method of producing an oral film-form base, comprising
dissolving or dispersing, in an organic solvent having a solubility parameter of 9.7 or higher, one or more edible polymers soluble in water and the organic solvent, and at least one compound selected from the group consisting of mono- to hexasaccharide sugars and sugar alcohols, wherein the at least one compound is in the form of a particle having an average particle size of 0.1 μm to 60 μm, and
forming a thin layer of the resulting dispersion and then drying the layer.

9. A method of producing an oral film-form preparation, comprising
dissolving or dispersing, in an organic solvent having a solubility parameter of 9.7 or higher, a drug, one or more edible polymers soluble in water and the organic solvent, and at least one compound selected from the group consisting of mono- to hexasaccharide sugars and sugar alcohols, wherein the at least one compound is in the form of a particle having an average particle size of 0.1 μm to 60 μm, and
forming a thin layer of the resulting dispersion, and then drying the layer.

10. A method of producing an oral film-form base, comprising:
dissolving, in a portion of an organic solvent having a solubility parameter of 9.7 or higher, one or more edible polymers soluble in water and the organic solvent to prepare a solution;
mixing the solution with a dispersion prepared by dispersing, in the rest of the organic solvent having a solubility parameter of 9.7 or higher, at least one compound selected from the group consisting of mono- to hexasaccharide sugars and sugar alcohols, wherein the at least one compound is in the form of a particle having an average particle size of 0.1 μm to 60 μm, to prepare a mixed dispersion; and
forming a thin layer of the dispersion, and then drying the layer.

11. A method of producing an oral film-form preparation, comprising:
dissolving, in a portion of an organic solvent having a solubility parameter of 9.7 or higher, one or more edible polymers soluble in water and the organic solvent to prepare a solution;
mixing the resulting solution with a dispersion prepared by dissolving or dispersing, in the rest of the organic solvent having a solubility parameter of 9.7 or higher, a drug and at least one compound selected from the group consisting of mono- to hexasaccharide sugars and sugar alcohols, wherein the at least one compound is in the form of a particle having an average particle size of 0.1 μm to 60 μm, to prepare a mixed dispersion; and
forming a thin layer of the dispersion, and then drying the layer.

\* \* \* \* \*